United States Patent [19]

Morris

[11] Patent Number: 4,470,264

[45] Date of Patent: Sep. 11, 1984

[54] LIFE SUPPORT APPARATUS FOR HUMAN BLOOD AND COMPOSITIONS THEREOF

[75] Inventor: Stanley D. Morris, Tucson, Ariz.

[73] Assignee: Engineering & Research Associates, Inc., Tucson, Ariz.

[21] Appl. No.: 483,779

[22] Filed: Apr. 11, 1983

[51] Int. Cl.³ .......................... B65B 63/08; F25D 3/08
[52] U.S. Cl. ........................................... 62/60; 62/372; 62/457; 62/530
[58] Field of Search ............... 62/457, 529, 530, 371, 62/372, 60, 62; 215/13 R; 383/110

[56] References Cited

U.S. PATENT DOCUMENTS

| 1,899,892 | 2/1933 | D'Este et al. | 383/110 X |
| 1,937,263 | 11/1933 | Bubb | 383/110 X |
| 2,393,245 | 1/1946 | Hadsell | 62/457 X |
| 3,576,650 | 4/1971 | Underwood et al. | 62/60 X |
| 3,971,231 | 7/1976 | Derry | 62/457 X |

FOREIGN PATENT DOCUMENTS 2550038  3/1977  Fed. Rep. of Germany ........ 62/457

*Primary Examiner*—Lloyd L. King
*Attorney, Agent, or Firm*—Cahill, Sutton & Thomas

[57] ABSTRACT

A transportable self-contained life support apparatus steadily reduces in temperature whole blood collected from donors to a predetermined temperature range. The whole blood is kept live by maintaining the temperature of the blood within such range through conductive heat transfer to an adjacent coolant. The coolant, in a frozen state and having a freezing temperature just below the predetermined range, absorbs heat commensurate to/with its latent heat of fusion and precludes temperature excursion of the blood until all of the coolant has become liquid. Similarly, platelets, extracted from the blood, can be maintained at the predetermined temperature range during storage and transport. Over chilling is precluded by limiting the low temperature of the coolant to its freezing temperature and a life destroying temperature rise is self-evident by and can only occur after a complete change in the state of the coolant.

13 Claims, 4 Drawing Figures

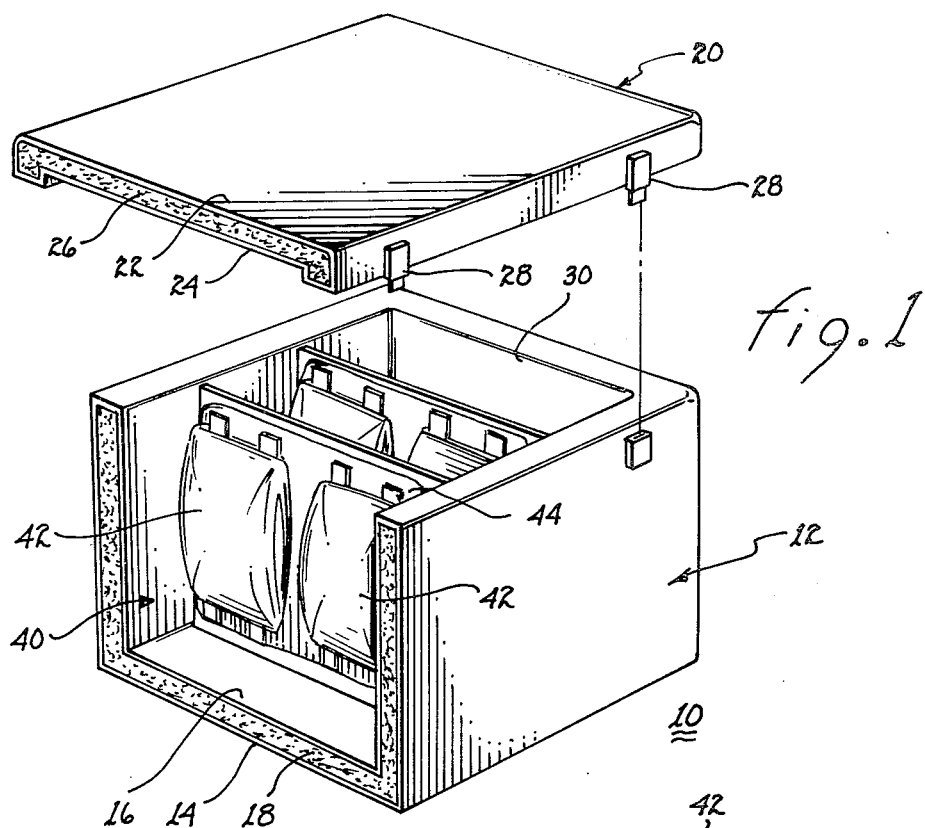
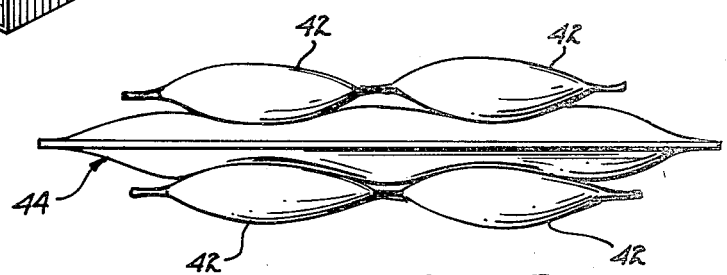
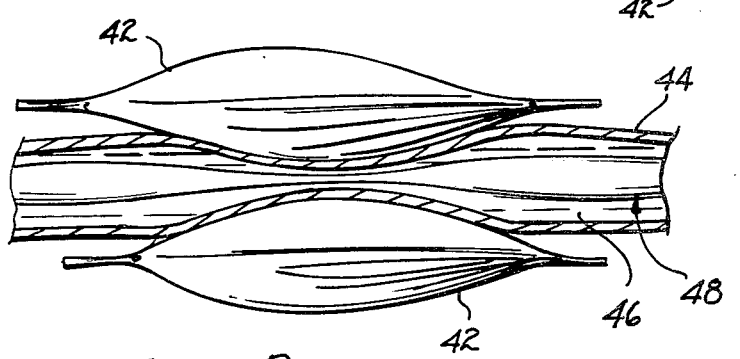
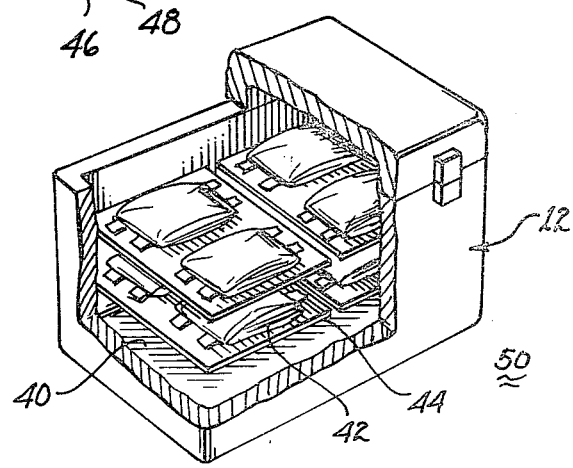
fig. 1
fig. 2
fig. 3
fig. 4

LIFE SUPPORT APPARATUS FOR HUMAN BLOOD AND COMPOSITIONS THEREOF

The present invention relates to life support apparatus and, more particularly, to life support apparatus for living organisms.

The recruitment of donors of blood is an ongoing campaign as the need for blood almost always is in excess of the supply. It is therefore mandatory to encourage the donation of whole blood and to make such donation as pleasant as possible for the donors. Various efforts along these lines have been undertaken by developments in blood collection equipment and by upgrading the quality of facilities used in conjunction with the donation of blood.

After a donation of blood, efforts must be undertaken to preserve the viability of the blood between the time of the donation and delivery to a blood processing facility. Failure to properly care for the donated blood will render the blood useless and the efforts to collect it will have been for naught.

Blood is a composition of living organisms, including red blood cells, plasma and platelets. These and other components are extracted from whole blood by a blood processing facility for later use in conjunction with surgery, human life preservation procedures and other medical and medicinal uses.

One of the most prevelant basis for deterioration or destruction of collected whole blood arises through failure to maintain certain temperature requirements during handling and transport. In particular, federal regulations attendant collection of whole blood require that the blood from which platelets are to be extracted be reduced in temperature steadily, and without any intermittent temperature rise, to a temperature in the range of 20° to 24° C. Such regulated temperature reduction and subsequent temperature maintenance will maintain viable the platelets and other constituents of the whole blood. In particular, the quality of the red cells will be maximized by maintaining the blood in this temperature range. Similarly, a concentrate of platelets separated from the blood at a processing facility must be maintained within a temperature range of 20° to 24° C. during transport to a transfusion hospital.

Certain efforts have been made to maintain and preserve the whole blood and components thereof, as evidenced by the following United States Patents. In U.S. Pat. No. 4,251,995 where is described a method for freezing platelets very rapidly to extremely low temperatures. U.S. Pat. No. 3,480,015 describes an electrically operated refrigeration unit employing a chilling convective air flow to draw heat from blood collection bags deposited within an insulated compartment. U.S. Pat. No. 4,194,369 is directed to apparatus having a pair of opposed flat plates for enclosing and cryogenically freezing a blood filled pouch. U.S. Pat. No. 2,467,268 describes a method for shipping chilled elements by alternately interleaving them with dry ice packs; thermal insulating means are disposed intermediate the item to be chilled and the dry ice to prevent heat transfer by conduction and resulting overchilling. U.S. Pat. No. 3,149,943 is directed to a chemically reactive refrigerant package for use primarily as a therapeutic device to prevent swelling of injured tissues. U.S. Pat. No. 3,282,068 is directed to a removeable heat absorbing chilled element locateable adjacent a container of goods to be chilled. U.S. Pat. No. 4,343,158 is directed to a pouch for storing insulin and includes thermal insulation and a refrigerant filled compartment to absorb heat; a further compartment is included within which a syringe for injection of the insulin may be stored.

The present invention is a life support apparatus for whole blood or segregated components thereof, such as platelets, which are maintained live. A coolant, having a specifically selected freezing point is disposed within a transparent pouch. Pouches of coolant are placed vertically on edge and interleaved with conventional collection bags for blood to locate the pouches and bags in direct physical contact with one another. The bags may be filled with whole blood or components thereof. An enclosing insulating container thermally shields the interleaved pouches and bags from the ambient environment. The coolant in each pouch is chilled to a temperature at or only a few degrees below its freezing temperature in order that its heat absorbtion be primarily a function of the latent heat of fusion of the coolant; thereby, the lowest possible temperature to which any adjacent bag can be subjected is the freezing temperature of the coolant. As a temperature gradient will exist across the material of the pouch and the material of the bag, the minimum temperature to which the bag contents will be chilled by the coolant will be a known number of degrees above the freezing temperature of the coolant. Moreover, the temperature of the coolant will be maintained fixed until a quantity of heat equivalent to the latent heat of fusion has been absorbed. Only thereafter can the temperature of the bag contents rise. The possibility of such a temperature rise and the resultant necessity for disposing of the bag contents, as its usefulness will have been jeopardized thereby, is immediately visually apparent if the coolant has changed completely from a solid to a liquid state.

It is therefore a primary object of the present invention to provide a life support apparatus for living organisms.

Another object of the present invention is to provide apparatus for maintaining whole blood or a concentrate of platelets live at a predetermined temperature range.

Yet another object of the present invention is to provide transportable apparatus for steadily reducing the temperature of blood to a predetermined range and maintaining the temperature of the blood within such range.

Still another object of the present invention is to provide self-contained and transportable apparatus for maintaining blood or a concentration of platelets within a predetermined temperature range.

A further object of the present invention is to provide a visually evident and immediately apparent indication of a potential or actual temperature rise of chilled blood or a chilled concentrate of platelets.

A yet further object of the present invention is to provide apparatus for drawing heat from blood or a concentrate of platelets by conduction without subjecting the blood or platelets to a life destructive low temperature.

A still further object of the present invention is to provide a method for chilling blood or compositions thereof to a predetermined temperature range by conductive heat transfer and maintaining the temperature of the blood or constituents thereof within the range.

These and other objects of the present invention will become apparent to those skilled in the art as the description thereof proceeds.

The present invention may be described with greater specificity and clarity with reference to the following drawings, in which:

FIG. 1 is an isometric cutaway view of apparatus for chilling and maintaining the temperature of blood or a component thereof within a predetermined range;

FIG. 2 is a top view illustrating heat transfer by conduction between bags containing blood or a component thereof and a coolant pouch;

FIG. 3 is a partial cross-sectional view illustrating the visually evident indication of whether the blood or a component thereof contained in a bag has been maintained within a predetermined temperature range; and FIG. 4 is a partial isometric cutaway view of a variant of the apparatus.

Referring to FIG. 1, there is shown a life support apparatus 10. The apparatus includes a thermally insulated container 12. As illustrated by the cutaway left portion, the construction of the container may include other and inner shells 14, 16 to provide a space therebetween. The space may be filled with air or a thermally insulating medium 18. Cover 20 may also be constructed with outer and inner shells 22, 24 segregated by an air filled space or by a thermally thermal insulating medium 26. Latches 28 may be used to secure the cover to the container. To minimize outflow of chilled air from within the container when open, access to the container is provided through a top opening 30.

The size and configuration of cavity 40 within container 12 is preferably selected to permit upright side by side positioning of two envelopes such as blood collection bags 42, which collection bags are also like those used to house a concentrate of platelets or other component of the blood. These collection bags are of industry standard size and configuration and are manufactured by any of several manufacturers. A pouch 44 is sized for placement in an upright orientation adjacent to and in contact with a pair of collection bags 42. The pouch is filled with a coolant chilled to a frozen state. Thereby, on initial insertion of pouch 44 within container 12, the pouch is rigid and serves in the manner of a heat sink. Additional pairs of collection bags and pouches are placed within cavity 40 in interleaved manner such that opposed sides of each collection bag is in physical contact with a pouch of coolant.

The heat transfer between a pouch and a collection bag is primarily through conduction, rather than the more common reliance upon convection. Such heat transfer permits effective control of the temperature difference between the contents of the collection bags and the coolant in the pouches as the thermal gradient across the respective bag and pouch membranes is readily determinable for the range of temperatures of interest. Thereby, by using conduction a very rapid cooling of the blood results. A reasonable degree of certainty of the temperature to which the bag contents will be cooled by the coolant is therefore available.

Whole blood contained within collection bags 42 is a composition of several different living organisms, including red blood cells, plasma and platelets. These organisms must be maintained live from the time they are withdrawn from a donor until they are transferred. In the case of concentrates of platelets, they must be maintained within a specified temperature range during storage and transport to a transfusion unit. The temperature of the living organisms during such interim storage and/or transportation is critical. To maintain the organisms viable, their temperature must be rapidly and steadily reduced from 37° C. (the normal body temperature) to a temperature in the range of 20° to 24° C. Federal regulations do not permit any intermittent temperature rise during an overall temperature reduction. Any blood which may have undergone such an intermittent temperature rise may have to be destroyed. A temperature drop below the range of 20° to 24° C. will have a detrimental effect upon the usefulness of some of the living organisms.

To meet these stringent criteria, elaborate and expensive devices requiring an external power source have been developed. The expense and complexity attendant such devices render them unuseable in many instances with a resultant loss of the possibility for receiving blood donations at remote collection locations due to attendant transport problems to a blood processing facility. Moreover, any malfunction of the power source of the complex components will jeopardize the viability of the affected blood. Most blood collection facilities are placing the collection bags filled with blood in a picnic basket-like container along with ice; the effectiveness of chill of the blood and reliability of steady temperature reduction is always in question.

In contradistinction, the present invention is the epitome of reliability and simplicity in number and operation of its components. Pouch 44 is filled with a proprietary coolant formulated to have a freezing temperature in the range of 18.6° to 19.5° C.; the amount of impurities in the coolant fluid accounts for the freezing point variation. Thus, pouches 44 can be frozen in a conventional refrigerator which is capable of maintaining a 35° to 50° F. temperature. Thus, equipment readily available to any user of the present invention can be employed to freeze and refreeze pouches 44. By knowing the thermal gradient and heat transfer characteristics across the membrane of pouch 44 and the adjacent contacting membrane of collection bag 42, the minimum temperature to which the contents within the bag can drop by heat transfer to the frozen coolant can be easily calculated. In one embodiment of the present invention, the contents of the collection bag will be maintained within a range of 20° to 24° C.

As pouch 44 absorbs heat, the coolant will begin to change state from a solid to a liquid. The resulting liquid will permit partial conformation of pouch 44 to the curved surface configuration of collection bags 42, as illustrated in FIG. 2. The resulting indentations in the pouch will tend to increase the contacting surface area 10 to 15% and promote further heat transfer by conduction over a larger surface area. In one embodiment wherein the contents of the collection bags is whole blood, the temperature of the blood drops from 37° to 20°–24° C. in 2 hours and is maintained at such temperature for 12 hours.

During transition of any fluid from a solid state to a liquid state, the temperature of the fluid will remain constant until there has been absorbtion of the latent heat of fusion attendant the fluid. Only after a complete change of state has been effected will the temperature of the fluid begin to rise.

Referring to FIG. 3, there is shown a pouch 42 wherein a portion of the coolant is in a liquid 46 while a remaining portion is still in a solid state 48. Such a composition is generally referred to as slush. The temperature of such slush is constant and at the freezing temperature.

Because of the constant temperature attendant a fluid undergoing a change of state, one can know with absolute certainty that the temperature of the fluid will not have risen until a change of state has been completed. This physical law provides an admirably efficient and clearly recognizeable indication of whether or not, after a period of time, the contents within bags 42 in container 12 have been maintained within the stipulated temperature range or whether the possibility has come about that the temperature of the contents of bags 42 may have risen above the predetermined temperature range. That is, if, after container 12 arrives at its destination or at such time as the bags are removed therefrom, any pouch 44 is totally liquid, a likelihood that the temperature of the coolant has risen above its freezing temperature exists. If that likelihood is present, and whether or not it has actually occurred, requires that the contents of the adjacent bags be discarded or tested. It is therefore inherent in the invention that a physical attribute of the coolant serves as a primary and readily apparent control on whether the integrity and quality of the contents of the bags has been maintained.

Often, platelets, a living organism segregated from blood and of great importance for the preservation of human life, is maintainable live by the present invention in the manner described above with respect to whole blood. Such transportation is not uncommon between a blood processing facility wherein the platelets are segregated and shipping to another facility for subsequent use.

In hot climates, where a shipment of blood may be exposed to temperature extremes, the present invention is of particular importance with respect to its vary obvious and clear quality control capabilities.

In known prior art devices, a heat absorbtion element or heat sink is generally maintained at a temperature substantially below that of the preferred temperature for the blood or constituents thereof. The inherent inefficiencies of such units are relied upon to ensure that the blood is not inadvertently chilled to a temperature below a predetermined range. For these devices, the amount of thermal insulation attendant the container and the ambient temperature become critical as they have an effect upon the efficiency of the heat transfer between the blood and the heat sink. Where such heat transfer is efficiently performed due to low ambient temperature or very efficient insulation of the unit, the temperature of the blood may drop below permissible levels. Moreover, heat transfer by convection or limited by insulating mediums between the blood and the heat sink are the norm. One of the attributes of the present invention is that it suffers none of these problems.

Referring to FIG. 4, there is shown a variant 50 of the apparatus and directed to the manner for placing pouches 44 and bags 42 within container 12. Herein, the pouches and bags are horizontally stacked. Such stacking is less preferred than a vertical upright arrangement since, due to inherent convection within cavity 40, the frozen pouches at the upper levels will liquify more rapidly than the pouches at the lower levels. Thus, a situation may arise wherein the coolant in one or more of the upper pouches may have changed to a liquid state while the coolant in the lower pouches may still be in a solid or slush state. One can therefore not be certain that each and every bag has been maintained uniformly at the preferred temperature range and has not experienced a temperature rise. Thus, the long term quality control available from the stacking arrangement illustrated in FIG. 1 is not as reliably available from the arrangement illustrated in FIG. 4.

In the above discussion, an assumption has been made that the ambient environment is at a temperature above 20°-24° C. If the ambient temperature is below this range, the invention may still be used with equally great effectiveness as a protectant against unnatural temperature drop. The coolant can be reformulated to have a freezing temperature of 26° C. and it would be placed in the container in a liquid state. The collection bags initially at a temperature of 20°-24° C. would be placed in the container. Any drop in temperature of the collection bags due to heat transfer through the container would result in a heat transfer from the protectant pouch to the bag. During such heat transfer the protectant would maintain a temperature of 26° F. and prevent a reduction in temperature of the bags below the 20°-24° C. range. This temperature stability would continue until the latent heat of fusion has been transferred and the protectant has undergone a change of state from liquid to solid. The quality control capability described above would also be present. That is, so long as some visually apparent liquid were present in the pouch the temperature of the bags would not have dropped below the range of 20°-24° C. Thus, the apparatus may be used as a portectant in very cold environments to maintain blood or its compositions within a predetermined temperature range.

While the principles of the invention has now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A method for maintaining live living organisms enclosed in an envelope and transported in temperature hostile environments, said method comprising the steps of:
   (a) placing the enveloped living organisms within a thermally insulated container;
   (b) locating a pouch of a coolant fluid as a heat sink within the container for drawing heat from the living organisms;
   (c) transferring heat from the living organisms to the heat sink by conduction in an amount equivalent to the latent heat of fusion of the coolant fluid to keep the living organisms within a predetermined temperature range; and
   (d) limiting the minimum temperature of the living organisms within the envelope to a temperature equivalent to the freezing temperature of the coolant fluid plus the temperature gradient across the walls of the envelope and the pouch.

2. The method as set forth in claim 1 including the step of determining for visual inspection exhaustion of the latent heat of fusion of the coolant fluid.

3. The method as set forth in claim 2 including the step of stacking within the container a plurality of envelopes and pouches in an interleaved relationship.

4. The method as set forth in claim 3 wherein said step of stacking includes the step of locating two envelopes vertically side by side adjacent at least one vertically oriented pouch.

5. A method for keeping live living organisms enclosed in an envelope and transported in temperature hostile environments, said method comprising the steps of:

(a) housing each envelope of the living organisms within a container;

(b) maintaining the living organisms within a predetermined temperature range within the container with a pouch housed coolant fluid by using the latent heat of fusion of the coolant fluid to effect heat transfer between the living organisms and the coolant fluid;

(c) transferring heat between the living organism and the coolant fluid primarily by conduction across the walls of the envelope and the pouch; and (d) displaying for visual inspection the state of the coolant fluid.

6. The method as set forth in claim 5 including the step of stacking the envelopes in interleaved relationship with pouches of coolant fluid.

7. A transportable life support apparatus for a living organism enclosed within an envelope:

(a) means for housing the envelope of living organisms;

(b) at least one pouch of coolant fluid, which coolant fluid has a freezing temperature point within a few degrees of a predetermined temperature range;

(c) means for maintaining the living organisms within the predetermined temperature range within said housing means with the coolant fluid by using the latent heat of fusion of the coolant fluid to effect heat transfer between the living organisms within the envelope and the coolant fluid within said pouch;

(d) means for transferring heat between the living organisms and the coolant fluid primarily by conduction through the walls of the envelope and said pouch; and (e) means for displaying for visual inspection the state of the coolant fluid.

8. The apparatus as set forth in claim 7 including a plurality of envelopes of living organisms, a plurality of said pouches, each said pouch containing a quantity of the coolant fluid and means for stacking the envelopes in interleaved relationship with said pouches.

9. A transportable life support apparatus for living organisms, which organisms can be maintained live if kept within a predetermined temperature range, said apparatus comprising in combination:

(a) a transportable thermally insulated closeable container for containing the living organisms;

(b) at least one envelope for housing the living organisms, said envelope being configured to fit within said container;

(c) heat sink means having a known freezing point at a temperature below a predetermined temperature range for maintaining the living organisms within the predetermined temperature range by being capable of absorbing from the living organisms a quantity of heat equivalent to the latent heat of fusion of said heat sink means, said heat sink means being configured to fit within said closed container; and (d) means for effecting a predictable heat transfer primarily between said envelope and said heat sink means;

whereby, the living organisms are maintained live by said heat sink means keeping the temperature of the living organisms within the predetermined temperature range.

10. The apparatus as set forth in claim 9 including visually apparent means attendant said heat sink means for readily determining the possibility of a rise in temperature of the living organisms above the predetermined temperature range.

11. The apparatus as set forth in claim 10 wherein said heat sink means comprises a pouch containing a coolant having a freezing point a few degrees below the predetermined temperature range and wherein said effecting means comprises the contacting walls of said envelope and said pouch, said walls having a temperature gradient there across equivalent to the difference in temperature between the freezing point of said coolant and a temperature within the predetermined range of temperature.

12. The apparatus as set forth in claim 11 wherein the heat transferred from said envelope to said pouch comprises at least a portion of the latent heat of fusion of said coolant.

13. The apparatus as set forth in claim 12 wherein said determining means comrises at least a transparent portion in said wall of said pouch to afford viewing of the state of said coolant.

* * * * *